United States Patent
von der Crone et al.

[11] Patent Number: 4,978,768
[45] Date of Patent: Dec. 18, 1990

[54] PROCESS FOR THE PREPARATION OF ALKYL ESTERS OF TETRACHLORO-2-CYANO-BENZOIC ACID

[75] Inventors: Jost von der Crone, Arconciel, Switzerland; Gonzague Overney, Glens Falls, N.Y.; Peter Dario, Choex, Switzerland

[73] Assignee: Ciba-Geigy Corporation, Ardsley, N.Y.

[21] Appl. No.: 1,311

[22] Filed: Jan. 8, 1987

[30] Foreign Application Priority Data

Jan. 15, 1986 [CH] Switzerland ............... 143/86

[51] Int. Cl.$^5$ .................................. C07C 255/50
[52] U.S. Cl. .................................... 558/416
[58] Field of Search ......................... 558/416

[56] References Cited

U.S. PATENT DOCUMENTS 3,803,202  4/1974  von der Crone ............... 558/416

FOREIGN PATENT DOCUMENTS 2112778  3/1970  Fed. Rep. of Germany ...... 558/416
853237  11/1960  United Kingdom ............... 558/416

OTHER PUBLICATIONS

Chem Abstracts; von der Crone et al., vol. 76, No. 3; 1413c (1972).
Sudarshan Chemical Ind. Ltd. Chem. Abstracts, vol. 97, No. 5, 38679u (1982).

Primary Examiner—John M. Ford
Assistant Examiner—J. Richter
Attorney, Agent, or Firm—JoAnn Villamizar

[57] ABSTRACT

Tetrachloro-2-cyanobenzoic acid alkyl esters of formula

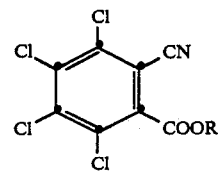

wherein R is $C_1$–$C_5$alkyl, can be very conveniently prepared by (a) reacting the ammonium salt of tetrachloro-2-cyanobenzoic acid, in the presence of water and an inert organic solvent, with a hydroxide of formula MOH, wherein M is Na or K, and removing the ammonia evolved, and (b) reacting the resultant salt of the formula

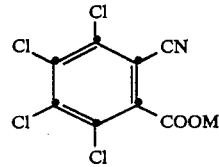

wherein M is as defined above, with at least 1 mole of a dialkyl sulfate of formula $SO_2(OR)_2$ or an alkyl halide of formula RHal, wherein R is as defined above and Hal is Cl, Br, I or F, also in the presence of water and an inert organic solvent.

10 Claims, No Drawings

PROCESS FOR THE PREPARATION OF ALKYL ESTERS OF TETRACHLORO-2-CYANO-BENZOIC ACID

The present invention relates to a process for the preparation of alkyl esters of tetrachloro-2-cyanobenzoic acid by alkylating the alkali metal salt of tetrachloro-2-cyanobenzoic acid obtained from the corresponding ammonium salt by direct reaction with sodium or potassium hydroxide.

It is known that alkyl esters of tetrachloro-2-cyanobenzoic acid are obtained by alkylating salts of tetrachloro-2-cyanobenzoic acid, which esters are important intermediates for the preparation of isoindolinone pigments.

Hitherto the alkylation has been carried out on an industrial scale as described in U.S. Pat. No. 3 803 202 with the ammonium salt of tetrachloro-2-cyanobenzoic acid, although the shortcomings of this process are considerable: on the one hand, an excessive consumption of alkylating agent, as the ammonium ion is also alkylated simultaneously, and, on the other, the formation of environmentally undesirable alkylsulfonic acid ammonium salts (as by-products), which have to be removed from the wastewater. The preparation of desired esters via silver, calcium or barium salts taught in GB Patent Specification 853 237 is also unsuitable, as it results in the formation of sparingly soluble silver, calcium or barium salts as by-products which cannot be separated direct from the final product. These disadvantages can be overcome by using an alkali metal salt, for it is necessary to use at most a small excess of alkylating agent and the alkali metal sulfonates obtained as by-products are readily soluble and environmentally harmless.

The reason why the much more suitable sodium salt of tetrachloro-2-cyanobenzoic acid has so far not been used for industrial manufacture of the esters is to be inferred from paragraph 2 of the above mentioned U.S. Pat. No. 3 803 202, where it is said that it is not possible to obtain a pure sodium salt from the ammonium salt of tetrachloro-2-cyanobenzoic acid by reaction with sodium hydroxide because of the secondary reactions and that it is therefore necessary to use ion exchangers (a very complicated method for large-scale production).

Surprisingly, it has now been found that the sodium salt of tetrachloro-2-cyanobenzoic acid is obtained in very good yield and good purity by reacting the corresponding ammonium salt, in the presence of water and an inert organic solvent, with sodium hydroxide solution. It has further been observed that the corresponding potassium salt obtained in analogous manner with potassium hydroxide is also suitable for the alkylation.

Accordingly, the present invention relates to a process for the preparation of tetrachloro-2-cyanobenzoic acid alkyl esters of formula I

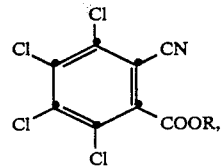

wherein R is $C_1$–$C_5$alkyl, which process comprises
(a) reacting the ammonium salt of tetrachloro-2-cyanobenzoic acid, in the presence of water and an inert organic solvent, with a hydroxide of formula MOH, wherein M is Na or K, and removing the ammonia evolved, and
(b) reacting the resultant salt of formula II

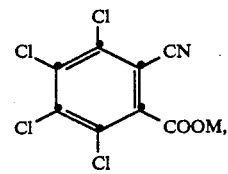

wherein M is as defined above, with at least 1 mole of a dialkyl sulfate of formula $SO_2(OR)_2$ or an alkyl halide of formula RHal, wherein R is as defined above and Hal is Cl, Br, I or F, also in the presence of water and an inert organic solvent.

Conveniently 1 to 1.5 moles of dialkyl sulfate or alkyl halide are used per mole of sodium or potassium salt of tetrachloro-2-cyanobenzoic acid.

R as $C_1$–$C_5$alkyl may be methyl, ethyl, n-propyl, isopropyl, n-butyl, sec-butyl, tert-butyl, n-pentyl and tert-pentyl, with ethyl being preferred and methyl most preferred.

M is preferably sodium and Hal is preferably chlorine.

The alkylating agent is preferably a dialkyl sulfate and is most preferably dimethyl sulfate.

Examples of inert organic solvents which may be suitably employed in the process of this invention, together with water, are aromatic hydrocarbons such as benzene, toluene, xylene, chlorobenzene, dichlorobenzene and nitrobenzene; aliphatic alcohols and ketones such as methanol, ethanol, isopropanol, methyl ethyl ketone and acetone; esters such as methyl and ethyl acetate; chlorinated aliphatic hydrocarbons such as carbon tetrachloride and/or methylene chloride; or petroleum fractions. Preferred solvents are toluene and methyl ethyl ketone. The same or different solvents can be used for both steps (a) and (b). It is preferred to use toluene for step (a) and methyl ethyl ketone for step (b).

Depending on the solvent, the volume ratio of water to inert organic solvent is from 1:3 to 3:1, but is preferably from 1:1.5 to 1.5:1.

The reaction temperature may vary from 10° to the boiling point of the solvent employed and is preferably in the range from 20° to 90° C. The preferred temperature range for reaction step (a) is from 20° to 30° C. and for reaction step (b) from 50° to 70° C.

The process is usually carried out under normal pressure or under slight overpressure.

The ammonium salt of tetrachloro-2-cyanobenzoic acid can be prepared by the method described in GB patent specification 853 237 by reacting 4,5,6,7-tetrachloro-3,3-phthaloyl chloride with aqueous ammonia. The ammonia evolved in reaction step (a) can be removed and recovered for preparing the ammonium salt.

The invention is illustrated by the following Example.

EXAMPLE 1

(a) Sodium salt of 3,4,5,6-tetrachloro-2-cyanobenzoic acid

In a reaction vessel, 398 g (3 moles) of 30% sodium hydroxide solution are added, with efficient stirring, over 30 minutes and at 40°–45° C. to a mixture of 302 g (1.0 mole) of the ammonium salt of 3,4,5,6-tetrachloro- 2-cyanobenzoic acid (reaction product obtained by reacting 4,5,6,7-tetrachloro-3,3-phthaloyl chloride with ammonia), 312 g of 25% aqueous ammonia and 400 g of toluene. The reaction mixture is stirred for 30 minutes at 20°–30° C., filtered on a suction filter, and the sodium salt of 3,4,5,6-tetrachloro-2-cyanobenzoic acid is washed in succession with toluene and water. Yield: 98% of theory, based on the ammonium salt of tetrachloro-2-cyanobenzoic acid.

(b) Methyl 3,4,5,6-tetrachloro-2-cyanobenzoate

A reaction vessel is charged in succession with 360 g of water, 475 g of methyl ethyl ketone and 307 g (1.0 mole) of the sodium salt (dry) of 3,4,5,6-tetrachloro-2-cyanobenzoic acid. With stirring, the mixture is heated to 72°–74° C. and to the suspension so obtained are added, at this temperature and over 1 hour, 189 g of dimethyl sulfate (1.5 moles), while keeping the pH at 5.0–5.5 by the gradual addition of 66 g (0.5 mole) of 30% sodium hydroxide solution. The reaction mixture is then stirred for 1 hour at reflux temperature (72°–74° C.). Conventional working up affords a yield of 93% of theory of methyl 3,4,5,6-tetrachloro-2-cyanobenzoate, based on the sodium salt of 3,4,5,6-tetrachloro-2-cyanobenzoic acid.

EXAMPLE 2

A reaction vessel containing 30 ml of water and 60 ml of methyl ethyl ketone is charged with 16.15 g of the dry potassium salt of 3,4,5,6-tetrachloro-2-cyanobenzoic acid. With stirring, the mixture is heated to 72°–74° C. and 9.45 g of dimethyl sulfate are added dropwise at the same temperature to the resultant suspension, while keeping the pH at 6–8 by the gradual addition of 30% potassium hydroxide solution. The reaction mixture is kept under reflux for 2 hours and the aqueous layer is then separated. The organic layer is completely evaporated, affording 12.4 g of methyl 3,4,5,6-tetrachloro-2-cyanobenzoate with a melting point of 82°–83° C.

EXAMPLE 3

The procedure of Example 2 is repeated, replacing dimethyl sulfate by 11.55 g of diethyl sulfate. Working up affords 15.9 g of crude product. Recrystallisation from ethanol affords 13.1 g of ethyl 3,4,5,6-tetrachloro-2-cyanobenzoate with a melting point of 74°–75° C.

EXAMPLE 4

12.9 g of the potassium salt of 3,4,5,6-tetrachloro-2-cyanobenzoic acid are heated for 20 hours under reflux in a mixture of 30 ml of water, 60 ml of methyl ethyl ketone and 11.4 g of methyl iodide. The aqueous phase is separated and the organic phase is concentrated by evaporation. Recrystallisation of the crude product (which contains only a small amount of impurities according to analysis by thin-layer chromatography) from ethanol affords 7.5 g of pure methyl 3,4,5,6-tetrachloro-2-cyanobenzoate with a melting point of 83°–84° C.

What is claimed is:

1. A process for the preparation of a tetrachloro-2-cyanobenzoic acid alkyl ester of formula I

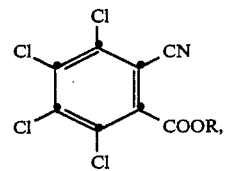

wherein R is $C_1$–$C_5$-alkyl, which process comprises
(a) reacting the ammonium salt of tetrachloro-2-cyanobenzoic acid, in the presence of water and an inert organic solvent, with a hydroxide of formula MOH, wherein M is Na or K, and removing the ammonia evolved, and
(b) reacting the resultant salt of formula II

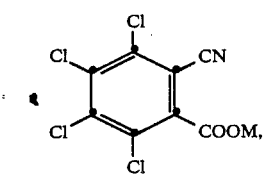

obtained substantially in pure form in step (a), wherein M is as defined above, with 1 to 1.5 moles of a dialkyl sulfate of formula $SO_2(OR)_2$ or an alkyl halide of formula RHal, wherein R is as defined above and Hal is Cl, Br, I or F per mole of said resultant salt of formula II, also in the presence of water and an inert organic solvent.

2. A process according to claim 1, wherein the hydroxide is NaOH.

3. A process according to claim 1, wherein the hydroxide is KOH.

4. A process according to claim 1, which comprises using a dialkyl sulfate of formula $SO_2(OR)_2$ or an alkyl halide of formula RHal, wherein R is methyl or ethyl and Hal is Cl.

5. A process according to claim 1, which comprises using a dialkyl sulfate of formula $SO_2(OR)_2$, wherein R is methyl.

6. A process according to claim 1, wherein the inert organic solvent is the same or different and is selected from toluene and methyl ethyl ketone.

7. A process according to claim 1, wherein toluene is used for step (a) and methyl ethyl ketone for step (b).

8. A process according to claim 1, wherein the process is carried out in the temperature range from 20° to 90° C.

9. A process according to claim 1, wherein the temperature range for reaction step (a) is from 20° to 30° C. and for reaction step (b) from 50° to 70° C.

10. A process according to claim 1, wherein the volume ratio of water to inert organic solvent is from 1:3 to 3:1.

* * * * *